United States Patent [19]

Kronenthal et al.

[11] Patent Number: 4,574,153
[45] Date of Patent: Mar. 4, 1986

[54] 8-OXO-2-OXA-1-AZABICYCLO(4.2.0)OCTANE-3-CARBOXYLIC ACIDS

[75] Inventors: David Kronenthal, Yardley, Pa.; Paula L. Kuester, West Trenton; William H. Koster, East Amwell Township, Hunterdon County, both of N.J.

[73] Assignee: E. R. Squibb & Sons, Inc., Princeton, N.J.

[21] Appl. No.: 707,357

[22] Filed: Mar. 1, 1985

[51] Int. Cl.$^4$ .............................. C07D 498/04
[52] U.S. Cl. ........................ 544/63; 260/239 A; 260/243.3; 548/110; 556/418; 556/419; 556/436
[58] Field of Search ................ 544/63; 260/243.3

[56] References Cited

U.S. PATENT DOCUMENTS 4,458,071 7/1984 Hall ........................... 544/90

OTHER PUBLICATIONS

Gleason et al., Journal of the American Chemical Society, 101 (16): pp. 4730-4731, (1979).
Woulfe et al., Tetrahedron Letters, vol. 25, No. 31, pp. 3293-3296, (1984).
Doyle et al., Can. J. Chem., vol. 58, (1980), pp. 2508-2523.

Primary Examiner—Richard L. Raymond

Attorney, Agent, or Firm—Lawrence S. Levinson; Donald J. Barrack

[57] ABSTRACT

Antibacterial activity is exhibited by compounds having the formula

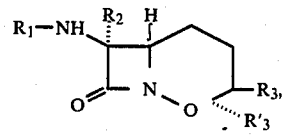

and pharmaceutically acceptable salts thereof, wherein, $R_1$ is an acyl group derived from a carboxylic acid; $R_2$ is hydrogen, methoxy, or formamido

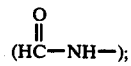

and
one of $R_3$ and $R'_3$ is hydrogen and the other is

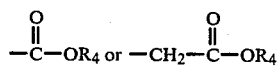

and $R_4$ is hydrogen alkyl, substituted alkyl, phenyl, substituted phenyl, phenylalkyl or (substituted phenyl)alkyl.

17 Claims, No Drawings

8-OXO-2-OXA-1-AZABICYCLO(4.2.0)OCTANE-3-CARBOXYLIC ACIDS

BRIEF DESCRIPTION OF THE INVENTION

Antibacterial activity is exhibited by compounds having the formula

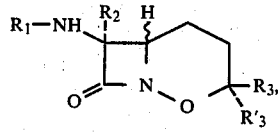

and pharmaceutically acceptable salts thereof. In formula I, and throughout the specification, the symbols are as defined below.

$R_1$ is an acyl group derived from a carboxylic acid; $R_2$ is hydrogen, methoxy, or formamido

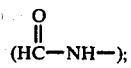

and
one of $R_3$ and $R'_3$ is hydrogen and the other is

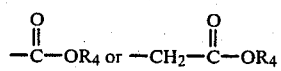

and $R_4$ is hydrogen alkyl, substituted alkyl, phenyl, substituted phenyl, phenylalkyl or (substituted phenyl)alkyl.

Listed below are definitions of various terms used to describe the compounds of this invention. The definitions apply to the terms as they are used throughout the specification (unless they are otherwise limited in specific instances) either individually or as part of a larger group.

The term "alkyl" and "alkoxy" refer to both straight and branched chain groups. Those groups having 1 to 10 carbon atoms are preferred.

The term "substituted phenyl" refers to phenyl substituted with 1, 2 or 3 halogen, hydroxy, carboxy, cyano, alkoxycarbonyl, aminocarbonyl, alkanoyloxy, trifluoromethyl, alkyl (of 1 to 4 carbon atoms) or alkoxy (of 1 to 4 carbon atoms) groups.

The term "halogen" refers to fluorine, chlorine, bromine and iodine.

The term "alkanoyloxy" refers to both straight and branched chain groups. Those groups having 2 to 10 carbon atoms are preferred.

The term "substituted alkyl" refers to alkyl groups substituted with one, or more, azido, amino, halogen, hydroxy, carboxy, cyano, alkoxycarbonyl, alkoxy, phenyloxy, (substituted phenyl)oxy, mercapto, alkylthio, phenylthio, (4,5,6 or 7-membered heterocycle)oxy, alkylsulfinyl or alkylsulfonyl groups.

The term "a 5, 6, or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetidinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, 2-furylidineimino, benzylideneimino or substituted alkyl, wherein the alkyl group has 1 to 4 carbon atoms, groups.

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein $R_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

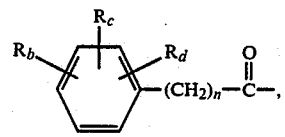

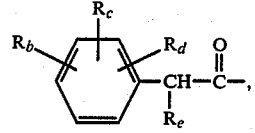

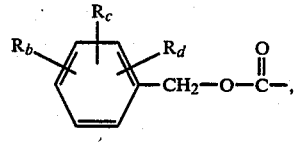

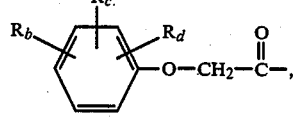

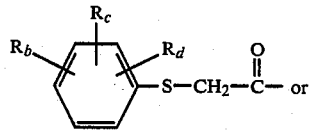

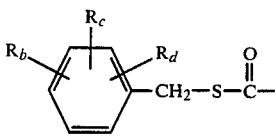

wherein n is 0, 1, 2 or 3; $R_b$, $R_c$, and $R_3$ each is independently hydrogen, halogen, hydroxyl, carboxy, nitro, amino, cyano, trifluoromethyl, aminocarbonyl, alkyl of 1 to 4 carbon atoms, alkoxy of 1 to 4 carbon atoms or aminomethyl; and $R_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

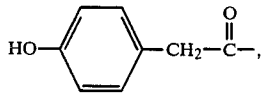

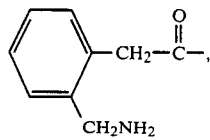

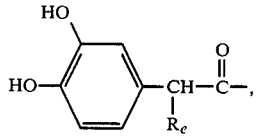

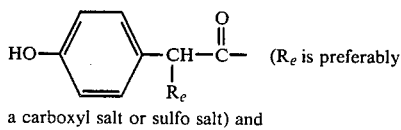 ($R_e$ is preferably a carboxyl salt or sulfo salt) and

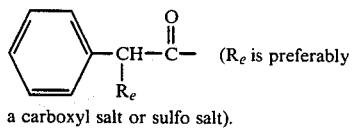 ($R_e$ is preferably a carboxyl salt or sulfo salt).

(c) Heteroaromatic groups having the formula

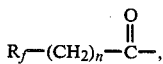

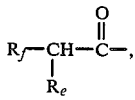

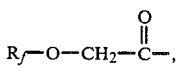

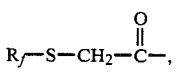

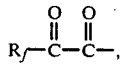

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or

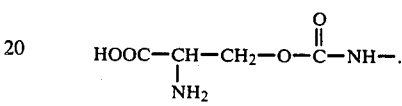

Preferred heteroaromatic acyl groups include those groups of the above formulas wherein $R_f$ is 2-amino-4-triazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula

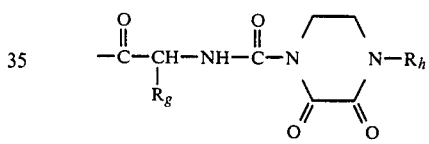

wherein $R_g$ is an aromatic group (including carbocyclic aromatics such as those of the formula

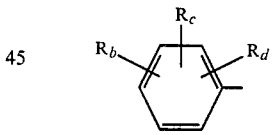

and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., $-N=CH-R_g$ wherein $R_g$ is as defined above), arylcarbonylamino (i.e.,

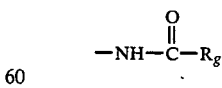

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula

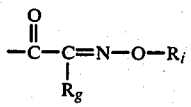

wherein $R_g$ is as defined above and $R_i$ is hydrogen, alkyl, cycloalkyl, alkylaminocarbonyl, arylaminocarbonyl (i.e.,

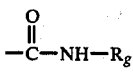

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula

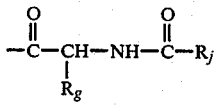

wherein $R_g$ is as defined above and $R_j$ is

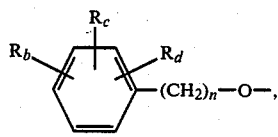

amino, alkylamino, (cyanoalkyl)amino, amido, alkylamido, (cyanoalkyl)amido,

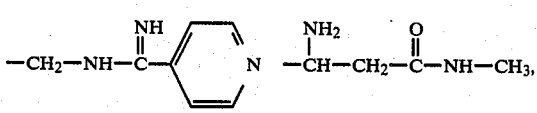

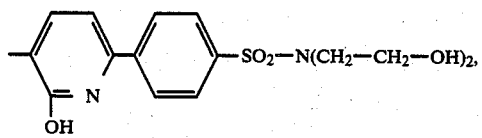

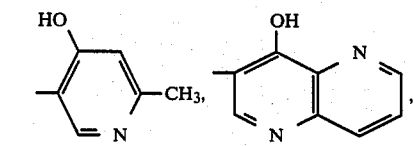

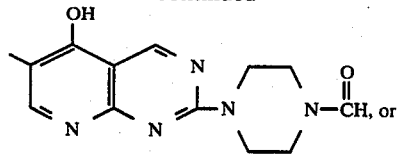

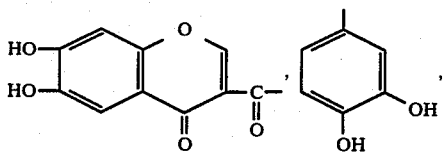

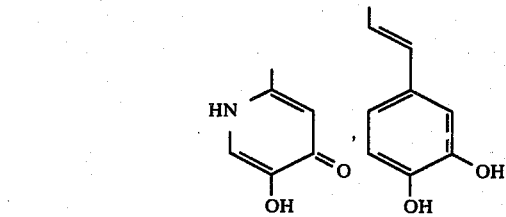

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

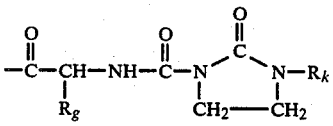

wherein $R_g$ is as defined above and $R_k$ is hydrogen, alkylsulfonyl, arylmethyleneamino (i.e., $-N=CH-R_g$ wherein $R_g$ is as defined above),

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The compounds of formula I form salts with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in a conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

DETAILED DESCRIPTION OF THE INVENTION

The β-lactams of formula I, and salts thereof, have activity against a range of gram-negative and gram-positive organisms. The compounds of this invention can be used as agents to combat bacterial infections (including urinary tract infections and respiratory infections) in mammalian species, such as domesticated animals (e.g., dogs, cats, cows, horses, and the like) and humans.

For combating bacterial infections in mammals a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the compounds of this invention. Such methods of administration include oral, intravenous, intramuscular, and as a suppository.

The compounds of this invention can be prepared starting with a dioxolane having the formula

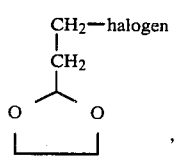
II wherein bromine is the preferred halogen. Treatment of a compound of formula II with magnesium, or with lithium or t-butyllithium, followed by sonication and reaction with acrolein at a reduced temperature, yields the compound having the formula

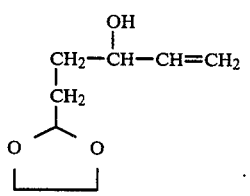
III

Sequential treatment of a compound of formula III with a catalyst, such as dimethylaminopyridine, and an organic base, such as triethylamine, followed by reaction with a protecting group, such as t-butylhalodiphenylsilane (preferably t-butylchlorodiphenylsilane) yields the compound having the formula

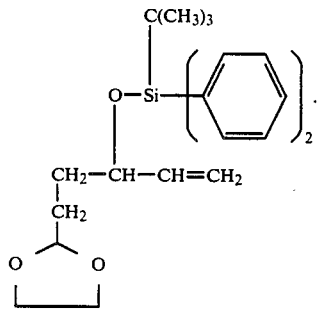
IV

Treatment of a compound of formula IV with an organic acid, such as p-toluenesulfonic acid, and water, yields the compound having the formula

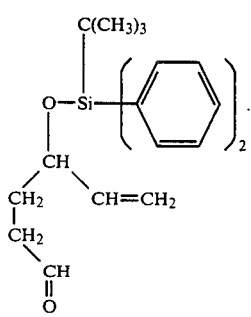
V

Alternatively, a compound of formula V can be prepared by treating the compound having the formula

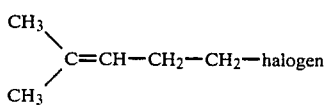
VI with t-butyllithium and then reacting it with acrolein to yield the compound having the formula

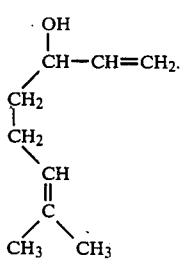
VII

Reaction of a compound of formula VII with a protecting group such as t-butylhalodiphenylsilane (preferably t-butylchlorodiphenylsilane) yields the compound having the formula

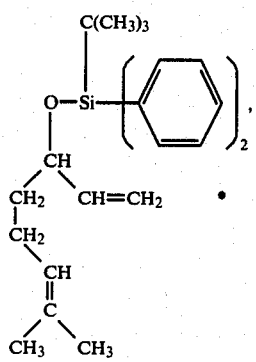

which can be subjected to selective ozonolysis to yield the compound of formula V.

Reaction of a compound of formula V with the lithium enolate of N,N-bis(trimethylsilyl)glycine trimethylsilyl ester at reduced temperature, followed by sequential treatment with ethanolic hydrogen chloride and an inorganic base yields the compound

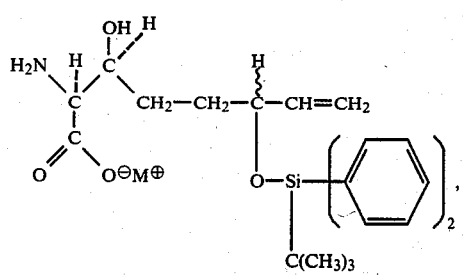

wherein $M^{\oplus}$ is a cation.

Protection of the amino group of the compound of formula IX can be accomplished using conventional techniques. Well-known protecting groups (referred to hereinafter as $A_1$) can be used; benzyloxycarbonyl is the preferred protecting group. The resulting compound has the formula

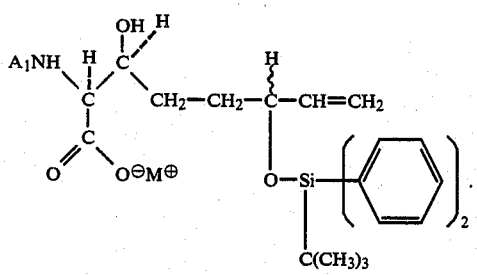

Reaction of a compound of formula X with a hydroxylamine having the formula

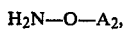

wherein $A_2$ is a protecting group such as triphenylmethyl, yields a compound having the formula

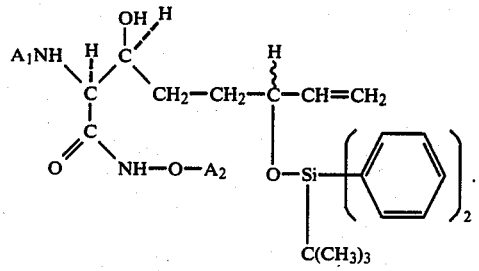

The reaction proceeds most readily if the carboxyl group of the compound of formula X is first activated and a coupling agent is present.

Ring closure of a compound of formula XII can be accomplished by treating a compound of formula XII with triphenylphosphine and diethylazodicarboxylate, and yields a compound having the formula

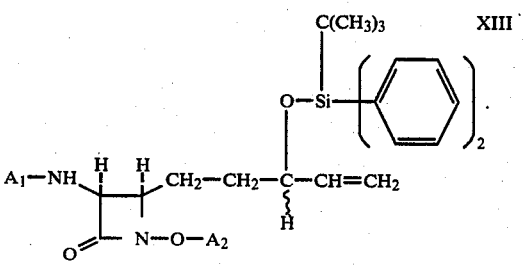

Other redox procedures can also be used to convert a compound of formula XII to a compound of formula XIII; e.g., triphenylphosphine, carbon tetrachloride and triethylamine can be used.

An olefin of formula XIII can be treated with ozone in the presence of methanol, and subsequently treated with dimethylsulfide to yield a compound having the formula

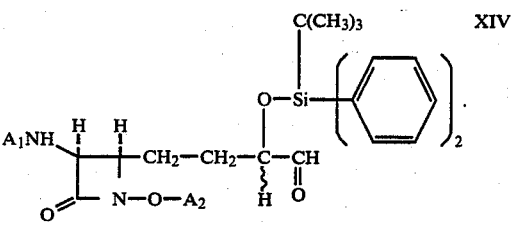

Oxidation of an aldehyde of formula XIV with ruthenium tetroxide yields the corresponding carboxylic acid having the formula

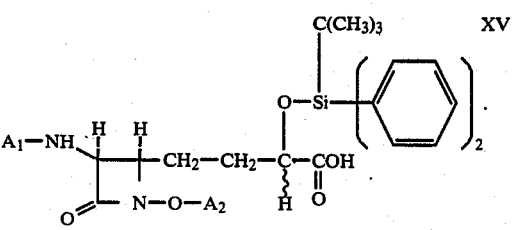

Protection of the carboxyl group of a compound of formula XV can be accomplished using conventional techniques. Well known protecting groups (referred to hereinafter as $A_3$) can be used; benzyl is the preferred protecting group. The resulting compound has the formula

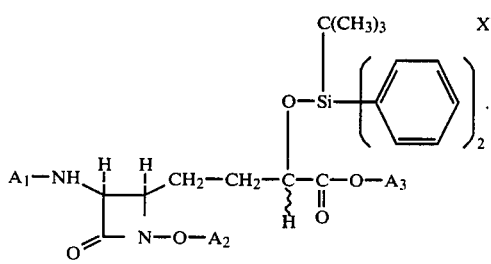

Treatment of a compound of formula XVI with tetrabutylammonium fluoride and acetic acid yields a compound having the formula

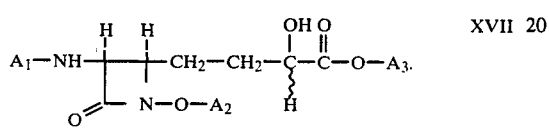

The hydroxyl group of a compound of formula XVII can be converted to a leaving group (referred to hereinafter as "OL", e.g. a tosylate or mesylate), and the resultant compound treated to remove the "$A_2$" protecting group. The particular deprotection reaction will, of course, depend on the "$A_2$" group present. For example, if the "$A_2$" group is trityl, treatment with acetic acid will cleave the group. The resultant compound has the formula

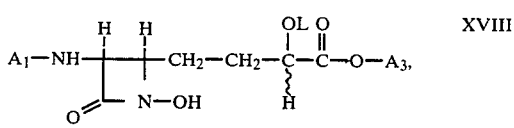

and can be cyclized by treatment with a base such as potassium carbonate to yield a mixture of compounds having the formulas

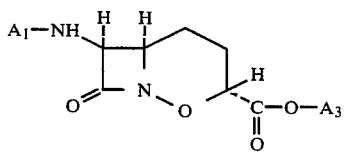

and

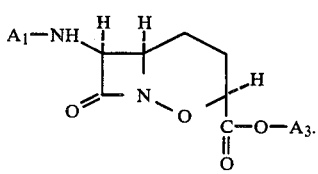

The compounds of formulas XIX and XX are separable by silica gel chromatography.

Alternatively, a mixture of compounds of formulas XIX and XX can be prepared by treating a compound of formula XVII with acetic acid to obtain a compound having the formula

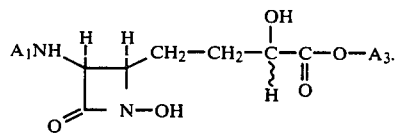

Subjecting a compound of formula XXI to redox conditions (e.g., triphenylphosphine and diethylazodicarboxylate) yields the desired compounds of formulas XIX and XX as a mixture.

Deprotection of a compound of formula XIX or XX using conventional techniques yields a key intermediate having the formula

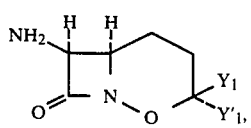

wherein one of $Y_1$ and $Y'_1$ is hydrogen and the other is

The compounds of formula XXII are novel compounds, and as such, they form an integral part of this invention.

Well known acylation techniques can be used to convert a compound of formula XXII to a product of formula I wherein $R_2$ is hydrogen and one of $R_3$ and $R'_3$ is hydrogen and the other is

i.e., a compound having the formula

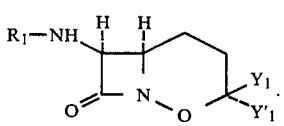

Exemplary techniques include reaction with a carboxylic acid ($R_1$—OH) or corresponding carboxylic acid halide or carboxylic acid anhydride. The reactions with a carboxylic acid proceed most readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group ($R_1$) contains reactive functionality (such as amino or carboxyl groups), it may be necessary to first protect these functional groups, then carry out the acylation reaction, and finally deprotect the resulting product.

Compounds corresponding to those of formula XXIII, but having the hydrogen substituent in the 6-position in the β-configuration, can be prepared by treating an aldehyde of formula V with an α-isocyanoacetic acid, alkyl ester to yield a compound having the formula

XXIV

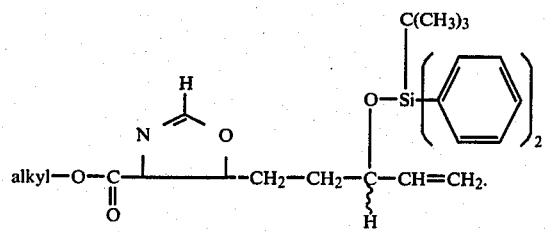

Treatment of a compound of formula XXIV with ethanolic hydrogen chloride yields the corresponding compound having the formula

XXV

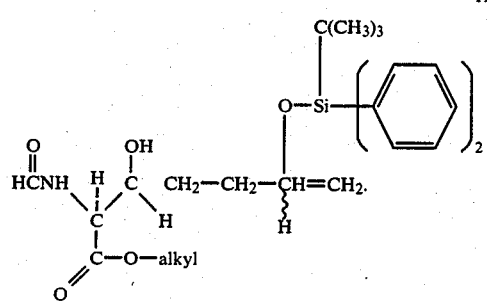

Treatment of a compound of formula XXV with an organic acid, such as hydrated p-toluenesulfonic acid, yields the corresponding amino compound having the formula

XXVI

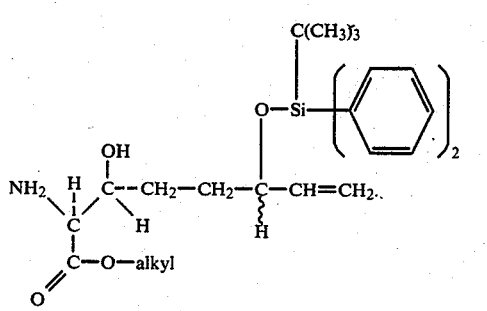

Treatment of a compound of formula XXVI with an inorganic base, methanol and water, yields the carboxylic acid salt having the formula

XXVII

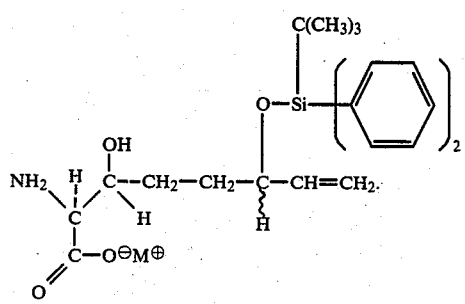

Following the procedure used to convert a compound of formula IX to an intermediate of formula XXII and product of formula XXIII, a compound of formula XXVII can be converted via intermediates having the formulas

XXVIII

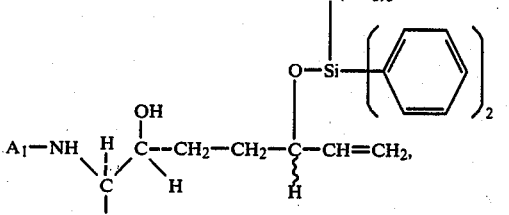

XXIX

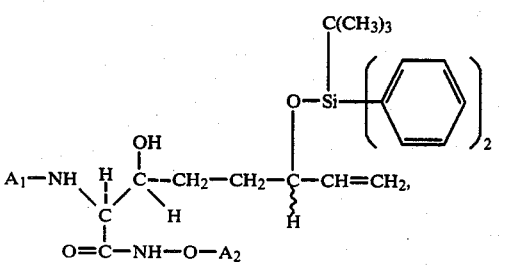

XXX

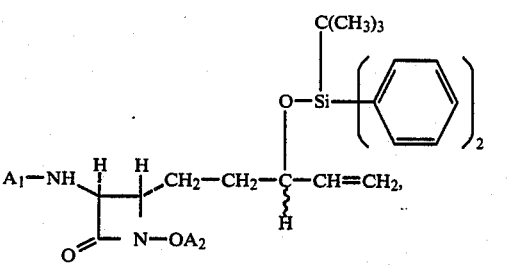

to an intermediate having the formula

XXXI

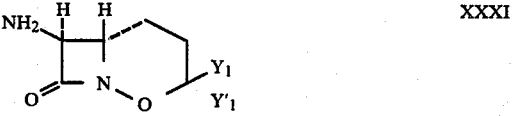

and product having the formula

XXXII

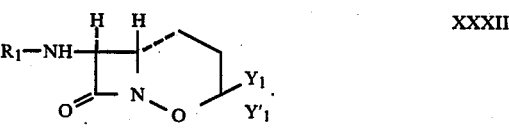

The products of formula I wherein one of $R_3$ and $R'_3$ is

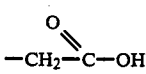

can be prepared by first treating a compound of formula XIII with tetrabutylammonium fluoride and acetic acid to yield a compound having the formula

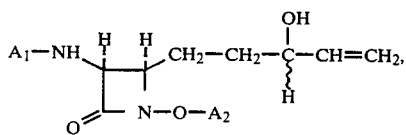

XXXIII which, if A₂ is acid labile (e.g., trityl) can be cyclized by treatment with trifluoroacetic acid to yield a mixture of compounds having the formulas

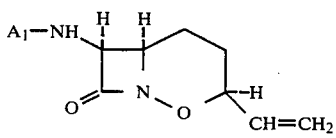

XXXIV and

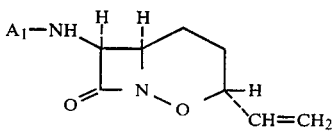

XXXV

Sequential treatment of a compound of formula XXXIV or XXXV with diborane and Jones Reagent yields the corresponding compound having the formula

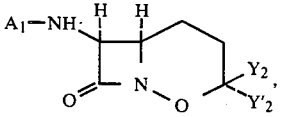

XXXVI wherein one of $Y_2$ and $Y'_2$ is hydrogen and the other is

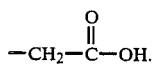

Deprotection of a compound of formula XXXVI using conventional techniques yield a key intermediate having the formula

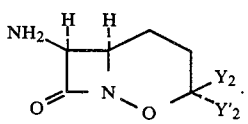

XXXVII

The compounds of formula XXXVII are novel compounds, and as such, they form an integral part of this invention.

Well known acylation techniques (exemplified above) can be used to convert a compound of formula XXXVII to a product of formula I wherein $R_2$ is hydrogen and one of $R_3$ and $R'_3$ is hydrogen and the other is

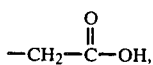

i.e., a compound having the formula

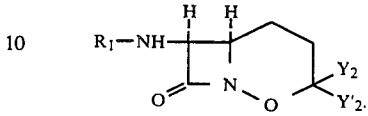

XXXVIII

Alternatively, a compound of formula XXXIII can be converted to a compound having the formula

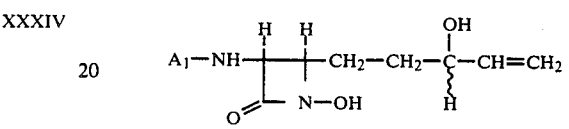

IXL which can be converted to a mixture of compounds having the formulas XXXIV and XXXV using trifluoroacetic acid or redox conditions.

Compounds corresponding to those of formulas XXXVIII, but having the hydrogen substituent in the 6-position in the β-configuration, can be prepared by first treating a compound of formula XXX with tetrabutylammonium fluoride and acetic acid to yield the corresponding compound having the formula

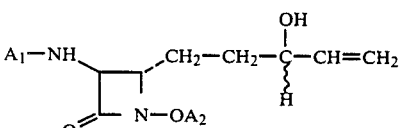

XL

Removal of the "A₂" protecting groups followed by cyclization of the resulting compound with triphenylphosphine, triethylamine and carbon tetrachloride yields a mixture of compounds having the formulas

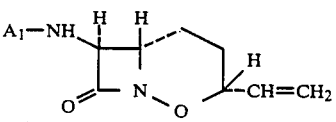

XLI and

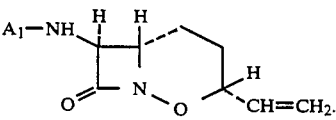

XLII

The compounds of formulas XLI and XLII are separable by silica gel chromatography.

Following the procedure used to convert a compound of formula XXXIV or XXXV to an intermediate of formula XXXVII and product of formula XXXVIII, a compound of formula XLI or XLII can be converted to an intermediate having the formula

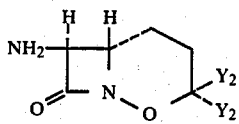

XLIII and then a product having the formula

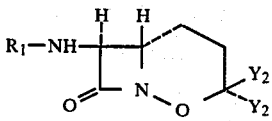

XLIV

Alternatively, a compound of formula XL can be converted to a mixture of compounds of formulas XLI and XLII using trifluoroacetic acid under anhydrous conditions if $A_2$ is an acid labile group such as trityl.

The products of formula I wherein one of $R_3$ and $R'_3$ is

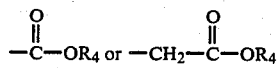

and $R_4$ is other than hydrogen can be prepared by alkylation of a salt of the corresponding carboxylic acid or by alternative esterification procedures (e.g., reaction of the carboxylic acid with an alcohol in the presence of a coupling agent).

The products of formula I wherein $R_2$ is methoxy can be prepared from the corresponding compound of formula XVI (or the corresponding $4\beta'$ hydrogen compound) wherein $A_1$—NH— is a carbamate (e.g., $A_1$ is benzyloxycarbonyl). Halogenation (preferably chlorination) of the urethane nitrogen yields a compound having the formula

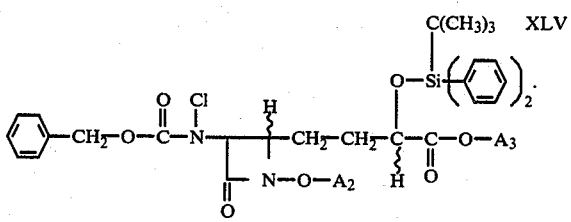

XLV

Reagents and procedures of N-chlorinating amides (urethanes) are known in the art. Exemplary reagents are tert-butyl hypochlorite, sodium hypochlorite, and chlorine. The reaction can be run in an organic solvent (e.g., a lower alkanol such as methanol) or in a two phase solvent system (e.g., water/methylene chloride) in the presence of a base such as sodium borate decahydrate. The reaction is run at a reduced temperature.

Reaction of a compound of formula XLV with a methoxylating agent, e.g., an alkali metal methoxide, yields a compound having the formula

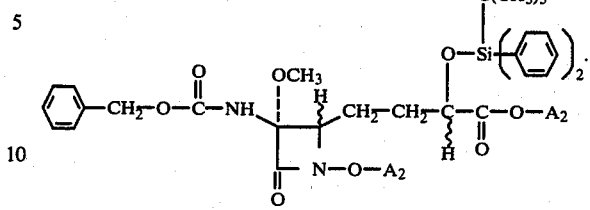

XLVI

Following the procedures described above for conversion of a compound of formula XVI to a product of formula I wherein $R_2$ is hydrogen, a compound of formula XLVI can be converted to the corresponding product of formula I wherein $R_2$ is methoxy.

Alternatively, a compound of formula XLVI can be prepared from a compound of formula XVI (or the corresponding $\beta$-hydrogen compound) wherein $A_1$ is a protecting group that can be selectively removed in the presence of the other protecting groups present in the molecule. Removal of the $A_1$ protecting group yields the corresponding compound having the formula

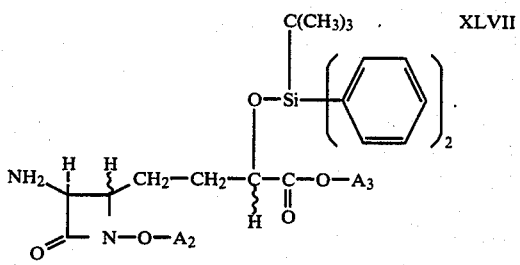

XLVII

Treatment of a compound of formula XLVII with an excess of a sulfenyl halide ($A_4$-S-halo, wherein $A_4$ is alkyl or aryl) such as p-toluenesulfenyl chloride or methanesulfenyl chloride in the presence of an acid scavenger yields a compound having the formula

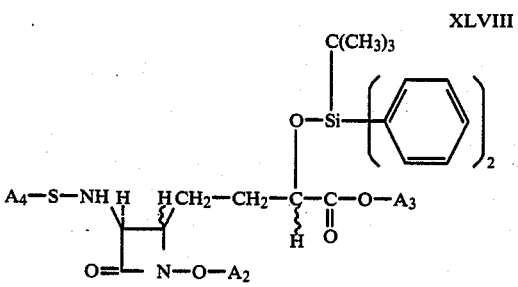

XLVIII which can be treated with triphenylphosphine, mercuric acetate and methanol in a halogenated solvent such as methylene chloride to yield a compound having the formula

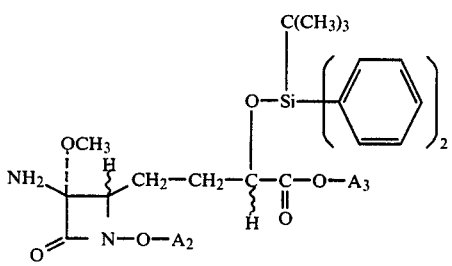

Acylation of a compound of formula IL with benzyl chloroformate yields the desired compound of formula XLVI.

The compounds of formula I wherein $R_2$ is formamido can be prepared from a compound of formula XLVIII. Treatment of the compound with triphenylphosphine and silica gel in methylene chloride effects rearrangement to a compound having the formula

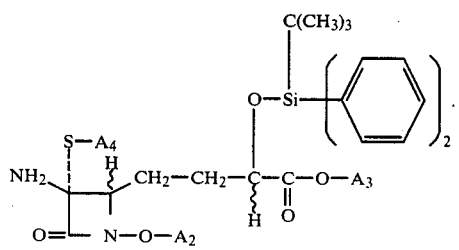

Acylation of a compound of formula L with benzyl chloroformate yields a compound having the formula

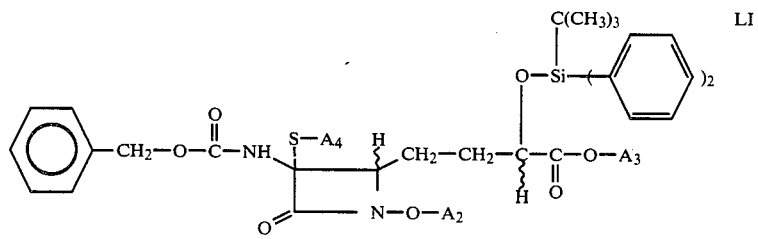

Treatment of a compound of formula LI with a nucleophilic derivative of formamide such as N,N-bis(trimethylsilyl)formamide in the presence of a thiophile such as mercuric acetate yields a compound having the formula

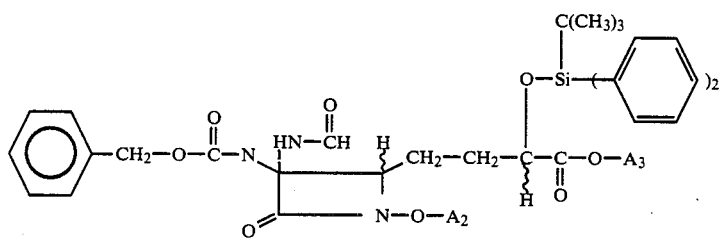

Following the procedures described above for conversion of a compound of formula XVI to a product of formula I, a compound of formula LII can be converted to the corresponding product of formula I wherein $R_2$ is formamide.

The following examples are specific embodiments of this invention.

EXAMPLE 1

[3α,6α,7β(Z)]-7-[[(2-Amino-4-thiazolyl)(methoxyimino)acetyl]amino]-8-oxo-2-oxa-1-azabicyclo[4.2.0]octane-3-carboxylic acid, monopotassium salt (A) α-Ethenyl-1,3-dioxolane-2-propanol A dry, 3-necked flask equipped with argon inlet, stirring bar, and dropping funnel was charged sequentially with magnesium turnings (1.047 g, 43.05 g-atom) and a solution of 2-(2-bromoethyl)-1,3-dioxolane (6 g, 33.14 mmole) in tetrahydrofuran (70 ml). The reaction vessel was placed in an ultrasonic cleaning bath and subjected to sonication for 2.5 hours with occasional swirling while maintaining the bath temperature at 25°-30° C. The brown mixture was then cooled to −78° C. and treated dropwise with freshly distilled acrolein (2.21 ml, 33.14 mmole) in tetrahydrofuran (15 ml). The resulting thick mixture was stirred at −78° C. for an additional 30 minutes, the cooling bath was replaced with an ice bath and the reaction was quenched with a saturated sodium sulfate solution (ca. 30 ml), followed by solid sodium sulfate. The clear supernate was decanted from the precipitated solids which were washed with ethyl acetate (3×100 ml). The combined washings were dried (sodium sulfate), filtered, and concentrated in vacuo of 4.28 g of oil. The crude product was chromatographed on 140 g of silica gel (230-400 mesh) with 40% ethyl acetate:hexane to afford 2.41 g of the title compound as a clear, colorless oil.

(B) 2-[3-[[(1,1-Dimethylethyl)diphenylsilyl]oxy]-4-pentenyl]-1,3-dioxolane

A solution of α-ethenyl-1,3-dioxolane-2-propanol (49.4 g, 315 mmole) in dichloromethane (175 ml) was treated sequentially with dimethylaminopyridine (5.72 g, 47 mmole) and triethylamine (52.8 ml, 380 mmole) followed by (dropwise) a solution of t-butylchlorodiphenylsilane (89.5 g, 332 mmole) in dimethylformamide (150 ml). The reaction was stirred under argon for 48 hours (25° C.), poured into 2.5 L of ice water and extracted with ethyl acetate (1.2 L). The organic extracts were wsashed with water (2×1 L), brine (1 L), dried (sodium sulfate), filtered, and concentrated in vacuo to 130 g of viscous yellow oil. The crude product was dissolved in ether, filtered from a small amount of suspended material, concentrated in vacuo, and chromatographed (Waters, Prep 500 L.C., 10% ethyl acetate:hexane) to afford 106 g of the title compound.

(C) 4-[[(1,1-Dimethylethyl)diphenylsilyl]oxy]-5-hexenal

A mixture of 2-[3-[[(1,1-dimethylethyl)diphenylsilyl]oxy]-4-pentenyl]-1,3-dioxolane (3.27 g, 8.24 mmole) and p-toluenesulfonic acid monohydrate (1.566 g., 8.24 mmole) in 3:1 acetone:water (24 ml) was stirred at 40° C. for 6 hours. The reaction was diluted with water and extracted with hexane. The extracts were washed with saturated potassium bicarbonate, water, brine, and dried (sodium sulfate). Filtration and concentration in vacuo produced 3.1 g of colorless oil which was a mixture of 2-[3-[[(1,1-dimethylethyl)diphenylsilyl]oxy]-4-pentenyl]-1,3-dioxolane and 4-[[(1,1-dimethylethyl)diphenylsilyl]oxy]-5-hexenal. The crude product was resubjected to the same reaction conditions and work-up as above. The crude product was chromatographed on silica gel (130 g, 230–400 mesh) with 5% ethyl acetate:hexane to afford 2.075 g of the title compound as a clear, colorless oil.

(D) (erythro)-2-Amino-3-hydroxy-6-[[(1,1-dimethylethyl)diphenylsilyl]oxy]-7-octenoic acid, monopotassium salt (mixture of C-6 epimers)

A solution of diisopropylamine (2.85 ml, 20.301 mmole) in tetrahydrofuran (55 ml) was cooled to −25° C. under an argon atmosphere and treated dropwise with n-butyllithium (12.5 ml of a 1.25M solution in hexane, 15.616 mmole). The resulting pale yellow solution was stirred for 20 minutes, cooled to −78° C. and treated dropwise with N,N-bis(trimethylsilyl)glycine, trimethylsilyl ester (4.34 g, 14.872 mmole). The resulting yellow solution was stirred for one hour and treated with a solution of 4-[[(1,1-dimethylethyl)diphenylsilyl]oxo]-5-hexenal (5 g, 14.164 mmole) in tetrahydrofuran (25 ml) dropwise over 45 minutes. The pale yellow solution was stirred at −78°0 C. for an additional hour and then at 0° C. for 1 hour. A solution of concentrated hydrochloric acid (4 ml) in ethanol (60 ml) was slowly added to the reaction (0° C.). Concentrated hydrochloric acid was then added until the pH of the mixture was 2.5. The pH was then raised to 10.5 with aqueous potassium carbonate, and most of the volatiles were removed in vacuo. Chloroform was added and removed in vacuo (repeated twice). Chloroform was added to the residue followed by hexane (to cloudiness) and the mixture was concentrated in vacuo (repeated twice). The residue was partitioned between water and chloroform. The aqueous layer was extracted with additional chloroform and the combined extracts were washed with concentrated potassium carbonate solution, dried (sodium sulfate), filtered, and concentrated in vacuo to 5 g of crude product which was chromatographed on 500 ml of HP-20 with 90% methanol:water. The fractions containing the desired material were combined and concentrated in vacuo. Traces of water were removed by dissolving the product in tetrahydrofuran, adding hexane to cloudiness, and evaporating (repeated twice). The yield of the title compound thus produced as a slightly yellow powder was 3.181 g.

(E) (erythro)-6-[[(1-Dimethylethyl)diphenylsilyl]oxy]-3-hydroxy-2-[[(phenylmethoxy)carbonyl]amino]-7-octenoic acid (mixture of C-6 epimers)

A solution of (erythro)-2-amino-3-hydroxy-6-[[(1,1-dimethylethyl)diphenylsilyl]oxy]-7-octenoic acid, monopotassium salt (mixture of C-6 epimers) (3.181 g, 6.841 mmole) and potassium bicarbonate (648 mg, 6.841 mmole) in tetrahydrofuran:water (70 ml, 1:1) was cooled to 0° C. and treated dropwise with benzyl chloroformate. The mixture was stirred for 2 hours and the pH was then lowered to 2.5 (from 6.5) with 0.6N hydrochloric acid. The mixture was extracted with ethyl acetate, the extracts were washed with brine, dried sodium sulfate, filtered and concentrated to 3.868 g of the title compound as a foam which was used directly in the next step.

(F) (erythro)-6-[[(1,1-Dimethylethyl)diphenylsilyl]oxy]-3-hydroxy-2-[[(phenylmethoxy)carbonyl]amino]-N-(triphenylmethoxy)-7-octenamide (mixture of C-6 epimers)

A solution of (erythro)-6-[[(1,1-dimethylethyl)diphenylsilyl]oxy]-3-hydroxy-2-[[(phenylmethoxy)carbonyl]amino]-7-octenoic acid (mixture of C-6 epimers) (3.645 g, 6.498 mmole), N-hydroxybenzotriazole hydrate (995 mg, 6.498 mmole), and O-tritylhydroxylamine (1.787 g, 6.5 mmole) in tetrahydrofuran (55 ml) was cooled to 0° C. under an argon atmosphere and treated dropwise over 15 minutes with a solution of dicyclohexyl carbodiimide (1.341 g, 6.5 mmole) in tetrahydrofuran (10 ml). The reaction was stirred an additional 10 minutes at 0° C., warmed to room temperature and stirred for 72 hours. Approximately half of the tetrahydrofuran was removed in vacuo and the residue was filtered to remove dicyclohexylurea. The filter cake was washed with tetrahydrofuran and the filtrate was evaporated. The residue was dissolved in ethyl acetate and the resulting solution was washed with saturated potassium bicarbonate, brine and dried sodium sulfate. Filtration and concentration in vacuo produced an oil that solidified upon treatment with ethyl acetate. The solid was filtered off and washed with cold ethyl acetate and hexane yielding 1.2 g of the desired hydroxamate. The filtrate was concentrated in vacuo to 4.75 g of oil which was chromatographed on 200 g of silica gel (230–400 mesh) with 75% hexane:ethyl acetate. Concentration of the appropriate fractions produced an additional 1.59 g of product. The total yield of the title compound was 2.79 g.

(G) 3,4-(cis)-4-[3-[[(1,1-dimethylethyl)diphenylsilyl]oxy]-4-pentenyl]-3-[[(phenylmethoxy)carbonyl]amino]-1-(triphenylmethoxy)-2-azetidinone (mixture of epimers)

A solution of (erythro)-6-[[(1,1-dimethylethyl)diphenylsilyl]oxy]-3-hydroxy-2-[[(phenylmethoxy)carbonyl]amino]-N-(triphenylmethoxy)-7-ocetenamide (mixture of C-6 epimers) (5.42 g, 6.623 mmole) and triphenylphosphine (5.266 g, 19.877 mmole) in tetrahydrofuran (150 ml) was cooled to −5° C. under an argon atmosphere and treated dropwise with a solution of diethylazaodicarboxylate (3.03 ml, 19.215 mmole) in tetrahydrofuran (20 ml). The temperature was warmed to 10° C. over 15 minutes at which point the cooling bath was removed and the reaction stirred for 1 hour at room temperature. The solvent was removed in vacuo and the residue was chromatographed on 400 g of silica gel (230–400 mesh) to yield 4.381 g of the title compound as a white solid.

(H) 3,4-(cis)-α-[[(1,1-dimethylethyl)diphenylsilyl]oxy]-4-oxo-3-[[(phenylmethoxy)carbonyl]amino]-1-(triphenylmethoxy)-2-azetidinebutanal (mixture of epimers)

A mixture of 3,4-(cis)-4-[3-[[(1,1-dimethylethyl)diphenylsilyl]oxy]-4-pentenyl]-3-[[(phenylmethoxy)carbonyl]amino]-1-(triphenylmethoxy)-2-azetidinone (mixture of epimers) (2.069 g, 2.59 mmole), potassium bicarbonate (258 mg, 0.259 mmole) and about 2 mg of Sudan III dye in 1:1 methanol:dichloromethane (90 ml) was cooled to −78° C. and ozonized until the dye faded. The reaction was purged with nitrogen. Dimethyl sulfide (20 ml, 25.9 mmole) was added at −78° C., the cooling bath was removed, and the reaction was stirred at room temperature for 2 hours, filtered and the solvents were removed in vacuo. Ethyl acetate was used to chase the methanol. The resulting oil was chromatographed on silica gel (100 g, 230-400 mesh) with 30% ethyl acetate:hexane to yield 1.463 g of the title compound as a white solid.

(I) 3,4-(cis)-α-[[(1,1-Dimethylethyl)diphenylsilyl]oxy]-4-oxo-3-[[(phenylmethoxy)carbonyl]amino]-1-(triphenylmethoxy)-2-azetidinebutanoic acid (mixture of epimers)

A mixture of 3,4-(cis)-α-[[(1,1-dimethylethyl)diphenylsilyl]oxy]-4-oxo-3-[[(phenylmethoxy)carbonyl]amino]-1-(triphenylmethoxy)-2-azetidinebutanal (mixture of epimers) (345 mg, 0.430 mmole) in 3:2:2 water-carbon tetrachloride:acetonitrile (2.1 ml, 1.4 ml, 1.4 ml) was stirred at room temperature. Sodium periodate (184 mg, 0.860 mmole) was added as a solid, followed by ruthenium dioxide hydrate (3.5 mg, 1% by weight based on starting material). The reaction was stirred vigorously for 1.5 hours at which point a gray-white precipitate formed. The reaction was diluted with 75 ml of ethyl acetate, washed with water (2×20 ml), brine (20 ml), dried (sodium sulfate), filtered, and concentrated in vacuo to a gray oil. The oil was chromatographed on silica gel (30 g, 230-400 mesh) eluting with 40% ethyl acetate:hexane to yield 158 mg of the title compound as a white solid.

(J) 3,4-(cis)-α-[[(1,1-Dimethylethyl)diphenylsilyl]oxy]-4-oxo-3-[[(phenylmethoxy)carbonyl]amino]-1-(triphenylmethoxy)-2-azetidinebutanoic acid, phenylmethyl ester (mixture of epimers)

A solution of 3,4-(cis)-α-[[(1,1-dimethylethyl)diphenylsilyl]oxy]-4-oxo-3-[[(phenylmethoxy)carbonyl]amino]-1-(triphenylmethoxy)-2-azetidinebutanoic acid (mixture of epimers) (553 mg, 0.676 mmole) in 5 ml of methylene chloride was stirred at room temperature. A solution of phenyl diazomethane in methylene chloride was added dropwise until a faint pink-orange color persisted and TLC verified that the reaction was complete. The reaction was quenched with a 20:1 methylene chloride-acetic acid solution until the pink color disappeared. The reaction was further diluted with 100 ml of methylene chloride, washed with potassium bicarbonate solution, dried (sodium sulfate), filtered and concentrated in vacuo to a viscous oil. The oil was chromatographed on silica gel (55 g, 230-400 mesh) eluting with 20% ethyl acetate:hexane to yield 401 mg of the title compound as a white solid.

(K) 3,4-(cis)-α-Hydroxy-4-oxo-3-[[(phenylmethoxy)carbonyl]amino]-1-(triphenylmethoxy)-2-azetidinebutanoic acid, phenylmethyl ester (mixture of epimers)

A solution of tetrabutylammonium fluoride in tetrahydrofuran (2.22 ml of 1M solution) was treated with acetic acid (158 μl, 2.77 mmole). The resulting solution was added to a solution of 3,4-(cis)-α-[[(1,1-dimethylethyl)diphenysilyl]oxy]-4-oxo-3-[[(phenylmethoxy)carbonyl]amino]-1-(triphenylmethoxy)-2-azetidinebutanoic acid, phenylmethyl ester (mixture of epimers) (499.5 mg, 0.555 mmole) in tetrahydrofuran (2.5 ml), and the reaction was stirred under argon at 45° C. for 2 hours. After cooling, the reaction was diluted with ethyl acetate (50 ml), washed with saturated potassium bicarbonate solution (2×10 ml), water (15 ml), brine (15 ml), dried (sodium sulfate), filtered and concentrated in vacuo. The resulting residue was chromatographed on silica gel (50 g, 230-400 mesh) eluting with 20% ethyl acetate:hexane to yield 311.5 mg the title compound as a white solid.

(L) 3,4-(cis)-α-[[(4-Methylphenyl)sulfonyl]oxy]-4-oxo-3-[[(phenylmethoxy)carbonyl]amino]-1-(triphenylmethoxy)-2-azetidinebutanoic acid, phenylmethyl ester (mixture of epimers)

A solution of 3,4-(cis)-α-hydroxy-4-oxo-3-[[(phenylmethoxy)carbonyl]amino]-1-(triphenylmethoxy)-2-azetidinebutanoic acid, phenylmethyl ester (mixture of epimers) (501 mg, 0.748 mmole) in dichloromethane (2 ml) was treated sequentially with triethylamine (156 μl, 1.122 mmole), p-toluensulfonyl chloride (157 mg, 0.822 mmole), and dimethylaminopyridine (9 mg, 0.075 mmole). The reaction was stirred at room temperature for 24 hours, concentrated in vacuo, and chromatographed on 45 g of silica gel (230-400 mesh) with 35% ethyl acetate:hexane, yielding 388 mg of the title compound.

(M) 3,4-(cis)-1-Hydroxy-α-[[(4-methylphenyl)sulfonyl]oxy]-4-oxo-3-[[(phenylmethoxy)carbonyl]amino]-2-azetidinebutanoic acid, phenylmethyl ester (mixture of epimers)

A solution of 3,4-(cis)-α-[[(4-methylphenyl)sulfonyl]oxy]-4-oxo-3-[[(phenylmethoxy)carbonyl]amino]-1-(triphenylmethoxy)-2-azetidinebutanoic acid, phenylmethyl ester (mixture of epimers) (388 mg, 0.480 mmole) in 43:7 acetic acid:water (5.5 ml) was stirred at room temperature for 30 minutes. The reaction was poured into an Erlenmeyer flask with 150 ml of ethyl acetate and 50 ml of saturated potassium bicarbonate solution. After gas evolution ceased, the organics were further washed with saturated potassium bicarbonate solution (50 ml), dried (sodium sulfate), filtered, and concentrated in vacuo to 342 mg of 3,4-(cis)-1-hydroxy-α-[[(4-methylphenyl)sulfonyl]oxy]-4-oxo-3-[[(phenylmethoxy)carbonyl]amino]-2-azetidinebutanoic acid, phenylmethyl ester (mixture of epimers) contaminated with triphenylcarbinol. NMR indicated a 1:1 mixture of the title compound and triphenylcarbinol.

(N) [3α,6α,7β]-8-Oxo-2-oxa-7-[[(phenylmethoxy)carbonyl]amino]-1-azabicyclo[4.2.0]octane-3-carboxylic acid, phenylmethyl ester and [3α,6β,7α]-8-oxo-2-oxa-7-[[(phenylmethoxy)carbonyl]amino]-1-azabicyclo[4.2.0]octane-3-carboxylic acid, phenylmethyl ester A solution of crude 3,4-(cis)-1-hydroxy-α-[[(4-methylphenyl)sulfonyl]oxy]-4-oxo-3-[[(phenylmethoxy)carbonyl]amino]-2-azetidinebutanoic acid, phenylmethyl ester (mixture of epimers) (340 mg, 1:1 mixture of 3,4-(cis)-1-hydroxy-α-[[(4-methylphenyl)sulfonyl]oxy]-4-oxo-3-[[(phenylmethoxy)carbonyl]amino]-2-azetidinebutanoic acid, phenylmethyl ester (mixture of epimers) and triphenylcarbinol, 0.416 mmole of tosylate) in dimethylformamide (5 ml) was stirred at 0° C. under argon and treated with solid potassium carbonate (172 mg, 1.248 mmole). After three hours, the reaction was diluted with methylene chloride (20 ml), dried (sodium sulfate), filtered, and concentrated in vacuo to yield a white gummy solid. Chromatography on silica gel (25 g, 230-400 mesh) afforded [3α,6α,7β]-8-oxo-2-oxa-7-[[(phenylmethoxy)carbonyl]amino]-1-azabicyclo[4.2.0]octane 3-carboxylic acid, phenylmethyl ester (68 mg) and [3β,6α,7β]-8-oxo-2-oxa-7-[[(phenylmethoxy)carbonyl]amino]-1-azabicyclo[4.2.0]octane-3-carboxylic acid, phenylmethyl ester (75.7 mg) as white solids.

(O) [3α,6α,7β(Z)]-7-[[(2-Amino-4-thiazolyl)(methoxyimino)acetyl]amino]-8-oxo-2-oxa-1-azabicyclo[4.2.0]octane-3-carboxylic acid, monopotassium salt A solution of [3α,6α,7β]-8-oxo-2-oxa-7-[[(phenylmethoxy)carbonyl]amino]-1-azabicyclo[4.2.0]octane 3-carboxylic acid, phenylmethyl ester (10.8 mg, 0.0263 mmole) in dimethylformamide (0.3 ml) was stirred under one atmosphere of hydrogen at room temperature in the presence of 10% palladium on carbon (10.8 mg) for thirty minutes. Concurrently, a mixed anhydride of (Z)-2-amino-α-(methoxyimino)-4-thiazoleacetic acid was prepared by treating the acid (5.3 mg, 0.0263 mmole) in 0.2 ml of dimethylformamide with diisopropylethylamine (5.0 μl), 0.0289 mmole) and stirring at room temperature under argon for five minutes. After cooling to −25° C., diphenylchlorophosphate (5.4 μl, 0.0263 mmole) was added and the reaction was stirred for thirty minutes. The hydrogenolysis reaction was cooled to −25° C. and the yellow mixed anhydride solution was transferred via syringe into the hydrogenation reaction. Diisopropylethylamine (15.3 μl, 0.0789 mmole) was added and after thirty minutes the reaction was warmed to 5° C. and stirred overnight (ca. 16 hours). The palladium catalyst was removed by filtration through Celite and the filtrate was concentrated in vacuo to a gray oil. The oil was dissolved in 5% acetone:water and chromatographed on Dowex (12 ml, 50×8-400 ion exchange resin, potassium form) eluting with water. After lyophilization, the resulting white solid was dissolved in water (pH adjusted to 7.0) and chromatographed on HP-20 resin (5 ml) eluting with water. The desired fractions were lyophilized to yield 6.0 mg of the title compound as a white solid.

IR (KBr): 1770, 1655, 1610 cm$^{-1}$.

NMR (D$_2$O): δ6.88 (S,1H), 5.12(d,J=4), 4.22(dd,J=12, 2 Hz), 4.02(m,1H), 3.92(S,3H), 2.19-2.14(m,1H), 2.03-1.98(m,1H), 1.81-1.78(m,1H), 1.68-1.6(m,1H).

M.S. (FAB): Exact mass calc'd for C$_{13}$H$_{15}$N$_5$O$_6$SK m/e 408.0380, found m/e 408.0382.

EXAMPLE 2

[3α,6β,7α(Z)]-7-[[(2-Amino-4-thiazolyl)(methoxyimino)acetyl]amino]-8-oxo-2-oxa-1-azabicyclo[4.2.0]octane-3-carboxylic acid, monopotassium salt A solution of [3β,6α,7β]-8-oxo-2-oxa-7-[[(phenylmethoxy)carbonyl]amino]-1-azabicyclo[4.2.0]octane-3-carboxylic acid, phenylmethyl ester (see Example 1N; 15.6 mg, 0.038 mmole) in dimethylformamide (0.3 ml) was stirred under one atmosphere of hydrogen at room temperature in the presence of 10% palladium on carbon (15.6 mg) for thirty minutes. Concurrently, a mixed anhydride of (Z)-2-amino-α-(methoxyimino)-4-thiazoleacetic acid was prepared by treating the acid (7.6 g, 0.038 mmole) in 0.4 ml of dimethylformamide with diisopropylethylamine (7.2 μl, 0.042 mmole) and stirring at room temperature under argon for five minutes. Diphenyl chlorophosphate (7.9 μl, 0.038 mmole) was added after cooling to −25° C. and the mixed anhydride reaction was stirred at −25° C. for thirty minutes. The hydrogenolysis reaction was purged with nitrogen, cooled to −25° C. and the yellow mixed anhydride solution was transferred via syringe into the hydrogenation reaction. Diisopropylethylamine (19.7 μl, 0.114 mmole) was added and after thirty minutes the reaction was warmed to +5° C. and stirred overnight (ca. 16 hours). The palladium catalyst was removed by filtration through Celite and the filtrate was concentrated in vacuo to a gray oil. The oil was dissolved in 5% acetone:water and chromatographed on Dowex 50×2-400 ion exchange resin (potassium form, 18 ml) eluting with water. After lyophilization, the resulting white solid was dissolved in water (pH adjusted to 7.0) and chromatographed on HP-20 resin (8 ml) eluting with water. The desired fractions were lyophilized to yield 7.6 mg of the title compound as a white solid.

IR(KBr): 1770, 1660, 1610 cm$^{-1}$.

NMR(D20) δ6.86 (S,1H), 5.07(d,J=4.3 Hz), 4.43(dd,J=5, 2 Hz), 4.07-4.02(m,1H), 3.9(s,3H), 2.27-2.23 (m,1H), 2.14-2.05 (m,1H), 1.78-1.71 (m,1H), 1.5-1.41 (m,1H).

M.S. (FAB): Exact mass calc'd for C$_{13}$H$_{15}$N$_5$O$_6$SK m/e 408.0380 found m/e 408.0384.

What is claimed is:

1. A compound having the formula

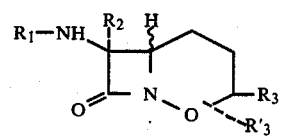

or a pharmaceutically acceptable salt thereof, wherein
R$_1$ is an acyl group derived from a carboxylic acid;
R$_2$ is hydrogen, methoxy, or formamido;
one of R$_3$ and R'$_3$ is hydrogen and the other is

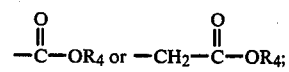

and
R$_4$ is hydrogen, alkyl, substituted alkyl, phenyl, substituted phenyl, phenylalkyl or (substituted phenyl)alkyl;
wherein the term "substituted alkyl" refers to alkyl groups substituted with one, or more, azido, amino, halogen, hydroxy, carboxy, cyano, alkoxycarbonyl, alkoxy, phenyloxy, (substituted phenyl)oxy, mercapto, alkylthio, phenylthio, (4, 5, 6 or 7-membered heterocycle)oxy, alkylsulfinyl or alkylsulfonyl groups; and
the term "substituted phenyl" refers to phenyl substituted with 1, 2 or 3 halogen, hydroxy, carboxy, cyano, alkoxycarbonyl, aminocarbonyl, alkanoyloxy, trifluoromethyl, alkyl of 1 to 4 carbon atoms or alkoxy of 1 to 4 carbon atoms groups.

2. A compound in accordance with claim 1 wherein R$_2$ is hydrogen.

3. A compound in accordance with claim 1 wherein R$_2$ is methoxy.

4. A compound in accordance with claim 1 wherein R$_2$ is formamido.

5. A compound in accordance with claim 1 wherein one of R$_3$ and R'$_3$ is hydrogen and the other is

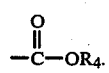

6. A compound in accordance with claim 5 wherein $R_4$ is hydrogen.

7. A compound in accordance with claim 1 wherein one of $R_3$ and $R'_3$ is hydrogen and the other is

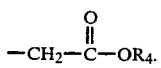

8. A compound in accordance with claim 7 wherein $R_4$ is hydrogen.

9. A compound in accordance with claim 2 wherein one of $R_3$ and $R'_3$ is hydrogen and the other is

10. A compound in accordance with claim 9 wherein $R_4$ is hydrogen.

11. A compound in accordance with claim 2 wherein one of $R_3$ and $R'_3$ is hydrogen and the other is

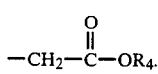

12. A compound in accordance with claim 11 wherein $R_4$ is hydrogen.

13. The compound in accordance with claim 1, [3α,6α,7β(Z)]-7-[[(2-amino-4-thiazolyl)(methoxyimino)acetyl]amino]-8-oxo-2-oxa-1-azabicyclo[4.2.0]octane-3-carboxylic acid, or a salt thereof.

14. The compound in accordance with claim 1, [3α,6β,7β(Z)]-7-[[(2-amino-4-thiazolyl)(methoxyimino)acetyl]amino]-8-oxo-2-oxa-1-azabicyclo[4.2.0]octane-3-carboxylic acid, or a salt thereof.

15. A compound in accordance with claim 1 wherein $R_1$ is

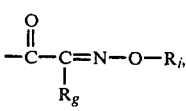

and $R_i$ is 1-carboxy-1-methylethyl or carboxymethyl and $R_g$ is 2-amino-4-thiazolyl.

16. A compound having the formula

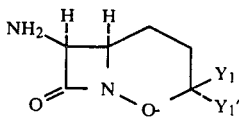

wherein one of $Y_1$ and $Y_1'$ is hydrogen and the other is

17. A compound having the formula

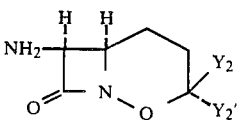

wherein one of $Y_2$ and $Y_2'$ is hydrogen and the other is

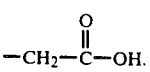

* * * * *

UNITED STATES PATENT AND TRADEMARK OFFICE
CERTIFICATE OF CORRECTION

PATENT NO. : 4,574,153

DATED : March 4, 1986

INVENTOR(S) : David Kronenthal et al.

It is certified that error appears in the above-identified patent and that said Letters Patent is hereby corrected as shown below:

Column 3, line 10, "$R_3$" should be -- $R_d$ --.

Column 4, line 26, "triazolyl" should be --thiazolyl--.

Signed and Sealed this

Fourteenth Day of October, 1986

[SEAL]

Attest:

DONALD J. QUIGG

Attesting Officer

Commissioner of Patents and Trademarks